(12) United States Patent
Proulx et al.

(10) Patent No.: US 7,963,919 B2
(45) Date of Patent: Jun. 21, 2011

(54) ULTRASOUND IMAGING TRANSDUCER ARRAY FOR SYNTHETIC APERTURE

(75) Inventors: Timothy L. Proulx, Santa Cruz, CA (US); Christopher M. Daft, Pleasanton, CA (US); J. Paul Mohr, Aptos, CA (US); Walter T. Wilser, Cupertino, CA (US); Charles E. Bradley, Burlingame, CA (US); Paul A. Wagner, El Cerrito, CA (US); Igal Ladabaum, San Carlos, CA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 1179 days.

(21) Appl. No.: 11/295,794

(22) Filed: Dec. 7, 2005

(65) Prior Publication Data

US 2007/0167752 A1   Jul. 19, 2007

(51) Int. Cl.
*A61B 8/00* (2006.01)
(52) U.S. Cl. ........ 600/447; 600/437; 600/443; 600/448; 600/446; 600/444
(58) Field of Classification Search ............... None
See application file for complete search history.

(56) References Cited

U.S. PATENT DOCUMENTS

| | | | |
|---|---|---|---|
| 4,204,435 A | 5/1980 | Bridoux et al. | |
| 4,817,434 A * | 4/1989 | Anderson | 73/625 |
| 4,831,601 A | 5/1989 | Breimesser et al. | |
| 5,389,848 A | 2/1995 | Trzaskos | |
| 5,744,898 A | 4/1998 | Smith et al. | |
| 5,851,187 A | 12/1998 | Thomas et al. | |
| 5,860,926 A | 1/1999 | Barabash et al. | |
| 5,901,708 A | 5/1999 | Chang et al. | |
| 5,938,612 A | 8/1999 | Kline-Schoder et al. | |
| 5,993,390 A | 11/1999 | Savord et al. | |
| 5,997,479 A | 12/1999 | Savord et al. | |
| 6,013,032 A | 1/2000 | Savord | |
| 6,048,315 A | 4/2000 | Chiao et al. | |
| 6,126,602 A | 10/2000 | Savord et al. | |
| 6,138,513 A | 10/2000 | Barabash et al. | |
| 6,159,153 A | 12/2000 | Dubberstein et al. | |
| 6,206,833 B1 | 3/2001 | Christopher | |
| 6,208,189 B1 | 3/2001 | Freeman et al. | |
| 6,251,073 B1 | 6/2001 | Imran et al. | |
| 6,309,356 B1 | 10/2001 | Ustuner et al. | |
| 6,352,510 B1 | 3/2002 | Barabash et al. | |
| 6,368,276 B1 | 4/2002 | Bullis | |

(Continued)

FOREIGN PATENT DOCUMENTS

EP   0 268 818 A1   6/1988

(Continued)

OTHER PUBLICATIONS

Sparse array imaging with spatially-encoded transmits, chiao et al.*

(Continued)

*Primary Examiner* — Tse Chen
*Assistant Examiner* — Joel F Brutus (57) ABSTRACT

Synthetic transmit aperture is provided for three-dimensional ultrasound imaging. A transducer may have separate transmit and receive elements. Broad beams are transmitted, allowing fewer transmit elements and/or more rapid scanning. A multidimensional receive array generates data in response to sequential transmissions, such as transmissions from different angles. The data is combined to increase resolution. A transducer array with offset transmit elements for forming a transmit line source may be used.

36 Claims, 5 Drawing Sheets

U.S. PATENT DOCUMENTS

| | | | |
|---|---|---|---|
| 6,380,766 B2 | 4/2002 | Savord | |
| 6,385,474 B1 * | 5/2002 | Rather et al. | 600/407 |
| 6,491,634 B1 | 12/2002 | Leavitt et al. | |
| 6,500,123 B1 | 12/2002 | Holloway et al. | |
| 6,506,160 B1 * | 1/2003 | Van Stralen et al. | 600/459 |
| 6,537,219 B2 | 3/2003 | Poland et al. | |
| 6,537,220 B1 * | 3/2003 | Friemel et al. | 600/447 |
| 6,551,246 B1 | 4/2003 | Ustuner et al. | |
| 6,569,102 B2 | 5/2003 | Imran et al. | |
| 6,605,043 B1 | 8/2003 | Dreschel | |
| 6,676,602 B1 | 1/2004 | Barnes | |
| 6,783,497 B2 | 8/2004 | Grenon et al. | |
| 6,790,182 B2 | 9/2004 | Eck et al. | |
| 6,806,623 B2 | 10/2004 | Petersen et al. | |
| 2002/0045830 A1 * | 4/2002 | Powers et al. | 600/459 |
| 2003/0149363 A1 | 8/2003 | Dreschel | |
| 2003/0163046 A1 * | 8/2003 | Nohara et al. | 600/443 |
| 2003/0171676 A1 * | 9/2003 | Trahey et al. | 600/441 |
| 2004/0064027 A1 * | 4/2004 | Zimmermann et al. | 600/407 |
| 2004/0267127 A1 | 12/2004 | Abend et al. | |
| 2005/0119575 A1 | 6/2005 | Ladabaum | |
| 2005/0124882 A1 | 6/2005 | Ladabaum et al. | |
| 2005/0124884 A1 | 6/2005 | Bolorforosh | |
| 2005/0148873 A1 | 7/2005 | Petersen et al. | |
| 2005/0148878 A1 | 7/2005 | Phelps et al. | |
| 2005/0154304 A1 | 7/2005 | Robinson | |
| 2005/0192499 A1 | 9/2005 | Lazenby et al. | |
| 2005/0203392 A1 | 9/2005 | Petersen et al. | |
| 2005/0215893 A1 | 9/2005 | Barnes et al. | |
| 2005/0243812 A1 | 11/2005 | Phelps | |
| 2005/0261589 A1 | 11/2005 | Daft et al. | |

FOREIGN PATENT DOCUMENTS

| | | |
|---|---|---|
| EP | 0 268 818 B1 | 6/1988 |
| EP | 1300690 | 4/2003 |
| EP | 1194920 | 7/2003 |
| EP | 1 391 875 A1 | 2/2004 |
| FR | 2 815 723 A1 | 4/2002 |
| WO | WO 0068931 | 11/2000 |

OTHER PUBLICATIONS

Maginness M. G., et al., 'State-of-the-art in Two-Dimensional Ultrasonic Transducer Array Technology', Medical Physics vol. 3, No. 5, Sep./Oct. 1976, pp. 312-318.

"Synthetic Transmit Aperture Imaging using Orthogonal Golay Coded Excitation," by Richard y. Chiao and Lewis J. Thomas; 2000 IEEE Ultrasonics Symposium; 4 pages.

"Optimizing Sparse Two-Dimensional Transducer Arrays Using an Effective Aperture Approach," by G. R. Lockwood and F.S. Foster; 1994 Ultrasonics Symposium; pp. 1497-1501.

"Application of Different Spatial Sampling Patterns for Sparse Array Transducer Design," by Svetoslav Ivanov Nikolov and Jorgen Arendt Jensen; Department of Information Technology, Center for Fast Ultrasound Imaging, Technical University of Denmark; Jun. 29, 1999; Ultrasonics 37 (2000); pp. 667-671.

"The Unifying Role of the Coarray in Aperture Synthesis for Coherent and Incoherent Imaging," by Ralph T. Hoctor, Member, IEEE and Saleem A. Kassam, Senior Member, IEEE; Proceedings of the IEEE, vol. 78, No. 4; Apr. 1990; pp. 735-752.

"Coarray Analysis of Wideband Pulse-Echo Imaging Systems," by Fauzia Ahmad and Saleem A. Kassam; Moore School of electrical Engineering, University of Pennsylvania, Philadelphia, PA; 1996 IEEE; pp. 3185-3188.

"Hybrid Multi/single Layer Array Transducers for Increased Signal-to-Noise Ration," by Richard L. Goldberg, et al.; 1997 IEEE Transactions on Ultrasonics, Ferroelectrics, and Frequency Control, vol. 44, No. 2; Mar. 1997; pp. 315-325.

"Zone-Based B-Mode Imaging," by David Napolitano et al.; 2003 IEEE Ultrasonics Symposium; pp. 25-28.

Excerpts from "Digital Image Processing," PIKS Inside, Third Edition by William K. Pratt; A Wiley-Interscience Publication; 2001; pp. 200-202.

Excerpts from "Algorithms, Complexity Analysis and VLSI Architectures for MPEG-4 Motion Estimation," by Peter Kuhn, Technical University of Munich, Germany; 1999 Kluwer Academic Publishers, Boston; pp. 30-31.

U.S. Appl. No. 10/834,779, filed Apr. 28, 2004.
U.S. Appl. No. 10/982,693, filed Nov. 5, 2004.
U.S. Appl. No. 10/819,094, filed Apr. 5, 2004.
U.S. Appl. No. 10/959,665, filed Oct. 4, 2004.
U.S. Appl. No. 11/152,632, filed Jun. 14, 2005.
Chiao, et al., "Sparse Array Imaging with Spatially-Encoded Transmits", 1997 IEEE Ultrasonics Symposium, pp. 1679-1682.

* cited by examiner

ULTRASOUND IMAGING TRANSDUCER ARRAY FOR SYNTHETIC APERTURE

BACKGROUND

The present embodiments relate to synthetic aperture beam forming. Broad transmit beams with synthetic aperture processing assist three-dimensional imaging.

Three-dimensional real-time imaging uses complex ultrasonic transducer arrays, transmit circuitry and/or receive circuitry. Simple array construction, sufficient power/acoustic transmission and density of electrical connection may be difficult to achieve.

In one approach for three-dimensional imaging, a one-dimensional array electronically steers along one dimension and is mechanically steered along another dimension (i.e., wobbler array). However, the mechanical scan may limit the speed for scanning an entire volume. The mechanism for moving the array may be large and/or complex, resulting in loss of comfort for the user or reduction in life of use.

In another approach, a one-dimensional array is translated or rotated by the user. This free hand scanning may degrade resolution. The position of the array is estimated or measured for rendering. The estimation may be inaccurate. The measurements may require additional hardware for use.

In another approach, elements of a two-dimensional array of discrete elements operate for both transmit and receive functions. Many limitations and complexities arise from such an approach. Each element is connected with transmit circuitry that is capable of supporting high drive voltages and power levels required to adequately insonify the area of interest. For a relatively small array of 32 by 32 elements, 1024 connections are needed. Direct connection of the elements with the system electronics via a cable bundle is impractical, so drive electronics may be positioned in the transducer housing. Positioning drive electronics in the transducer housing complicates packaging, and thermal dissipation issues limit the complexity of the drive electronics.

For receive operation, each element drives connecting cables or electronics. Pre-amplification near the elements may provide sufficient drive capability. Elements of an N by M array may be smaller than a typical one-dimensional array, making impedance matching of a single layer piezo-ceramic element to the transmission line very poor. Multilayered two-dimensional arrays may better match the impedance of the transmission line, but are difficult to construct. Additionally, the receive electronics must be isolated from the high voltage drive circuitry, requiring some type of transmit/receive switching at the array, diode isolation circuits or connections to both sides of the piezoceramic element, doubling the number of necessary connections.

Making a connection to each of several thousand transducer elements and placing beam-forming electronics in the transducer to reduce the number of cables may be achieved. Where partial beamforming within the transducer limits the number of cables, less channel information is provided. The available data for the imaging system is the partial beams. However, availability of the raw channel data may be important in a variety of clinical scenarios.

The speed of acquisition may be limited by requirements of spatial beam sampling and the sound speed in tissue. For a square transducer, if M beams fill a plane, at least $M^2$ beams fill a volume. A typical beam is 2 wavelengths wide, and a typical transducer may be 200 wavelengths long, giving M=100. A typical beam requires 0.2 ms to acquire. If Z focal zones are needed to improve coherence, a total of $M^2Z$ firings make up a volumetric image. For typical imaging depths, this results in a maximum imaging speed of $0.5/Z^2$ volumes per second. This speed may be insufficient for real-time three-dimensional imaging.

One technique to increase acquisition speed is used for two-dimensional imaging. Synthetic transmit aperture imaging or co-array imaging uses broad transmit beams to insonify an entire area of interest. Receive beams within the area of interest are formed in response to the single transmission.

BRIEF SUMMARY

By way of introduction, the preferred embodiments described below include methods and transducer systems for synthetic transmit aperture in ultrasound imaging. A transducer may have separate transmit and receive elements. Broad beams are transmitted, allowing fewer transmit elements and/or more rapid scanning. A multidimensional receive array generates data in response to sequential transmissions, such as transmissions from different angles. The data is combined to increase resolution. A transducer array with offset transmit elements for forming a transmit line source may be used.

In a first aspect, a method provides synthetic aperture with an ultrasound imaging transducer. First and second transmit elements sequentially transmit broad wavefronts. A receive array receives echoes responsive to the sequential transmissions. Elements of the receive array are separate from the transmit elements. Signals responsive to the echoes of the sequential transmissions are combined.

In a second aspect, a method provides synthetic aperture with an ultrasound imaging transducer. First and second transmit elements transmit broadly at different angles relative to a volume of interest. A multidimensional receive array receives echoes responsive to the sequential transmissions. Elements of the receive array are separate from the transmit elements. Signals responsive to the echoes of the sequential transmissions are combined.

In a third aspect, a method provides synthetic aperture with an ultrasound imaging transducer. First and second confocal data sets are acquired in response to sequential transmissions. The first and second confocal data sets each represent a full volume. The acquisition uses a fully sampled two-dimensional receive array. The first and second confocal data sets are synthesized.

In a fourth aspect, a transducer system for synthetic aperture in ultrasound imaging is provided. A transmit circuit causes at least two transmit elements to transmit acoustic energy in at least two plane or diverging wavefronts, respectively, in sequential transmissions. A multidimensional receive array of N receive elements has receive elements which are separate from the transmit elements. A receive circuit electrically connects with the receive elements. The receive circuit combines data representing a same volume and responsive to the sequential transmissions.

In a fifth aspect, an ultrasound transducer for synthetic aperture is provided. A second array of elements is offset from a first array. The second array of elements is operable to form a diverging wavefront with a focal region closer to the first array than the second array.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the FIG. 1 is a block diagram of one embodiment of a transducer system for synthetic transmit aperture processing with a multidimensional receive array.

DETAILED DESCRIPTION OF THE DRAWINGS AND PRESENTLY PREFERRED EMBODIMENTS

A two-dimensional transducer array includes one or more (e.g. 4) radiating ultrasound transmit elements and a distinct or separate highly sampled two-dimensional receive array. The receive array includes hundreds or thousands of receive elements. Sound waves are launched into the area of interest by sequentially firing each or groups of the transmit elements. The transmit elements produce a generally unfocused or weakly focused sound field, broadly illuminating a region of interest. By locating the transmit elements at different locations, sequential broad wavefronts propagate through the region of interest at different angles. The returning echoes are received by the receive array. Receive beams are formed from the echoes. Each acoustic sample in the region of interest is synthesized through summation of multiple beams from the multiple transmit operations. The two-way response represents a focused or conventional receive beam and an unfocused transmit beam. The transmit beam is (1) completely isotropic, (2) focused in azimuth but unfocused in elevation, or vice versa, or (3) partially focused in both azimuth and elevation. The summation is incoherent (compounding) or coherent (synthesis), or a combination of the two.

Synthetic aperture imaging combines this transmit aperture with a fully sampled receive aperture for three-dimensional imaging. Acquisition speed is increased as compared to focused transmit scanning. The resulting image is in-focus throughout the region of interest. The acquired data may include samples for the entire region.

Figure 1:
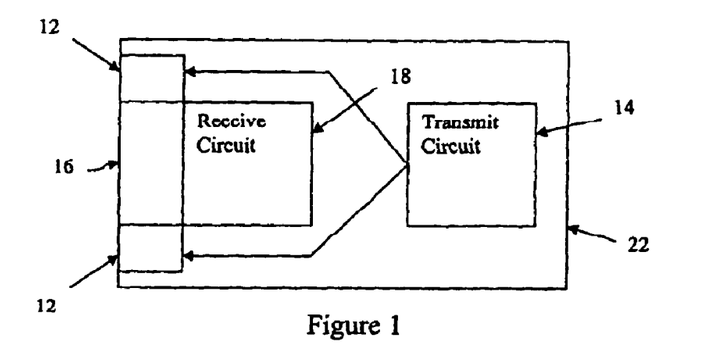

FIG. 1 shows a transducer system for synthetic aperture in ultrasound imaging. The transducer system includes transmit elements 12, a transmit circuit 14, a receive array 16, a receive circuit 18 and a transducer housing 22. Additional, different or fewer components may be provided. For example, the transducer housing 22 is not provided, or the transmit circuit 14 and/or all or a portion of the receive circuit 18 are outside of the transducer housing 22.

The transmit elements are piezoelectric elements, such as PZT slabs or composites. Alternatively, micromachined, capacitive, polyvinylidene di-fluoride (PVDF) or other materials operable to transduce from electrical to acoustic energy are used. In one embodiment shown in the side view of FIG. 2, the transmit elements 12 are multi-layer piezoceramic elements. Multiple layers may increase the electric field across each layer and output higher acoustic pressure for a given drive voltage compared to a single layer piezoceramic. In alternative embodiments, the transmit elements 12 are each a single layer of piezoceramic. Different or the same structures and/or materials are provided for each of the transmit elements 12.

Figure 2:
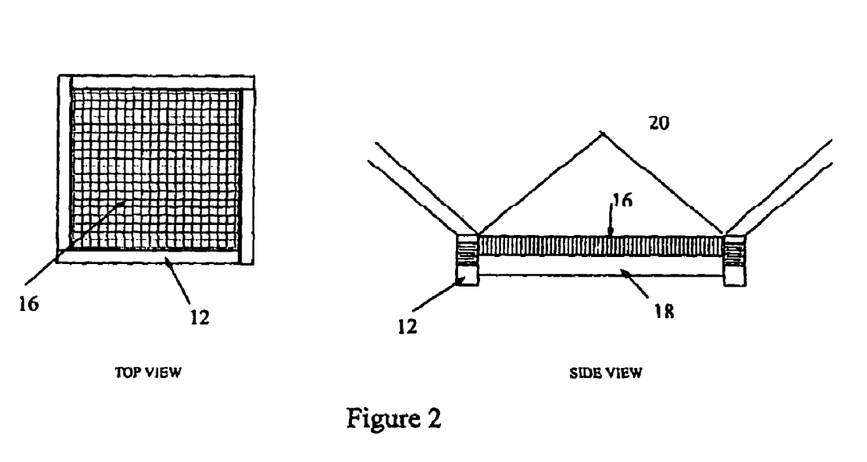
FIG. 2 shows top and side views of a transducer with separate transmit and receive elements in one embodiment.
Figures 4, 5:
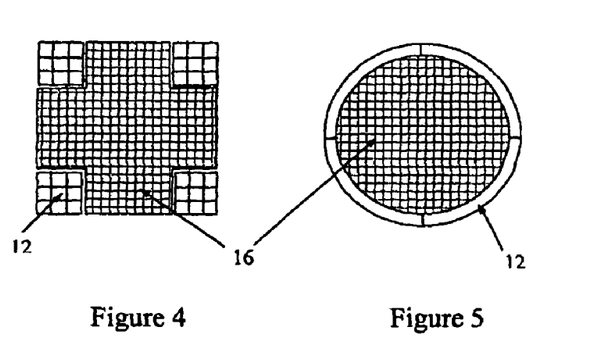

Each transmit element 12 is relatively large as compared to individual receive elements, but same or smaller sized transmit elements 12 may be used. FIG. 2 shows rectangular transmit elements 12 positioned at the perimeter of the receive array 14. Alternatively, square, hexagonal or some other shape transmit elements are positioned at the corners, center and/or elsewhere relative to the receive array 16. FIG. 5 shows a segmented ring defining the transmit elements 12 with the receive array 16 within the ring. Each transmit element 12 may be unfocused or propagate a diverging beam, illuminating a pyramid shaped volume 20 (see FIG. 2).

Figure 6:
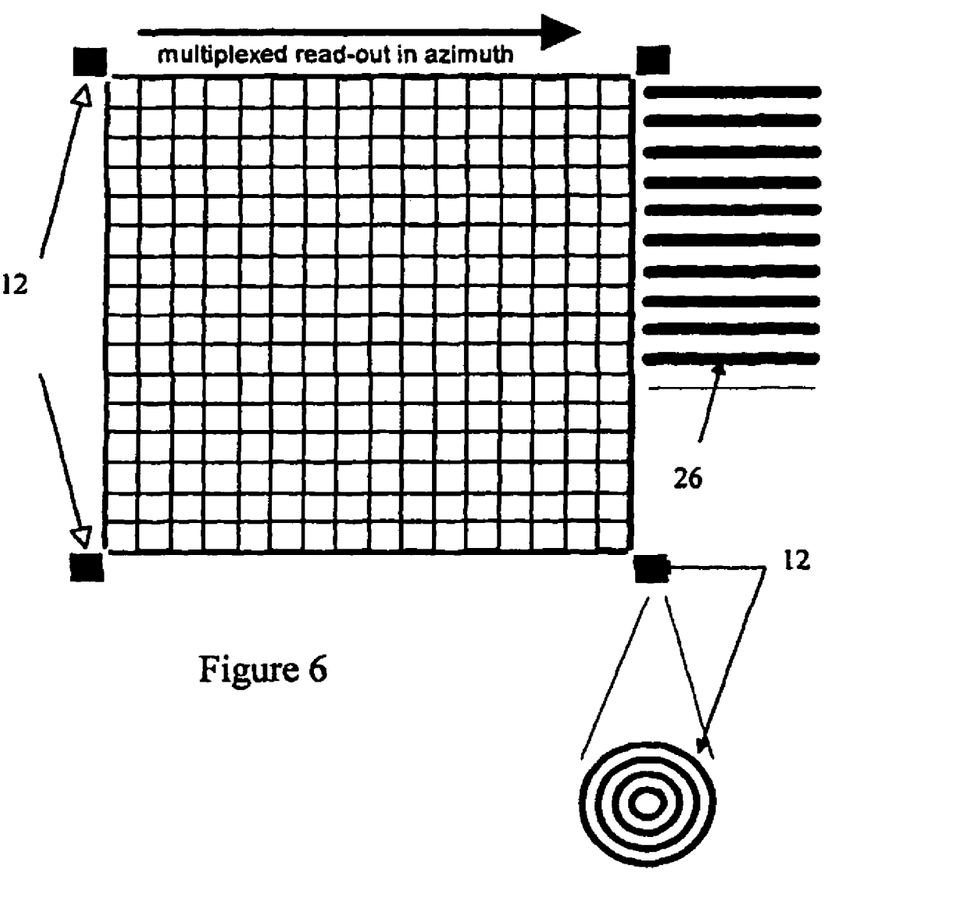

In alternative embodiments shown in FIGS. 4 and 6, the transmit elements 12 are small arrays. FIG. 4 shows a rectangular array of transmit elements 12. FIG. 6 shows annular arrays of transmit elements 12, such as annular arrays of 20 elements each. Transmit elements 12 formed as arrays may allow coarse or fine steering to concentrate on a particular region and reduce clutter. The transmit arrays may be used to transmit as a point source.

Figure 3:
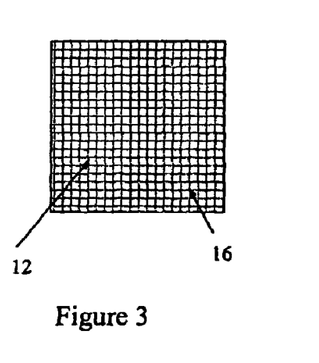
FIGS. 3-7 are top views of transducers with separate transmit and receive elements in other embodiments.

Two or more transmit elements 12 are used. Only one transmit element 12 may provided. The total number of transmit elements 12 is less than the total number of receive elements, such as being less than half the number of receive elements. FIGS. 2 and 5 show four transmit elements 12. FIG. 4 shows thirty six transmit elements 12. FIG. 3 represents a single transmit element 12, but a greater number of transmit elements 12 may be used.

The number of transmit connections with the transmit circuit 14 is reduced by several orders of magnitude from that of a two-dimensional transducer array with all of the elements used as both transmit and receive elements. Using a few transmit elements fired sequentially may reduce the heat generation in the transmit circuit 14 and allow higher transmit output. Additionally, the multi-layer architecture for the transmit elements 12 is simple to realize for the larger transmit elements 12. Due to the proportional increase in electric field with the number of layers, multilayer transmit elements 12 may output sufficient acoustic power with low voltage driven electronics or battery operation for a stand-alone device.

The transmit elements 12 are positioned adjacent to and/or within the receive array 16. Since the synthetic aperture is the convolution of the transmit aperture and the receive aperture, the transmit elements 12 are situated on the edges or adjacent to the receive array 16. FIGS. 2 and 5 show the transmit elements 12 surrounding a periphery of the receive array 16. FIGS. 4 and 6 show the transmit elements 12 at corners or opposite edges of the receive array 16. The transmit elements 12 are immediately adjacent receive elements, such as being separated by an air, gas, liquid, or solid filled kerf for acoustic isolation. Other acoustically isolating structures may be used, such as cured bonding agent for holding the transmit elements 12 adjacent to the receive array 16. The transmit elements 12 are formed from a same or different substrate as the receive array 16. Alternatively, a greater separation, such as a half or full wavelength gap is provided. The separation shown in FIGS. 7 and 8 may be even larger, such as tens of millimeters.

The transmit elements 12 do not overlap in azimuth or elevation with the receive array 16. In an alternative embodiment shown in FIG. 3, the transmit element 12 overlaps with the receive array 16 in elevation and azimuth, but is layered with the receive array 16 or does not overlap in a range dimension.

The transmit circuit 14 is a switch network, pulser, waveform generator, transmit beamformer, memory, digital-to-analog converter, beamformer or other now known or later developed circuit for generating ultrasound transmit waveforms. For example, the transmit circuit 14 is a switching bipolar or unipolar pulser with an amplifier for each transmit element 12. Alternatively, a fewer number of pulsers and amplifiers than transmit elements 12 is provided, such as multiplexing a single pulser and amplifier to different transmit elements 12 sequentially. The amplifier provides high drive voltages and power levels, such as for applying a transmit voltage of +/−200 volts.

The transmit circuit 14 is positioned in an imaging system and connects to the transmit elements 12 through cables, such as a coaxial cables. Alternatively, a portion or the entire transmit circuit 14 is within the transducer housing 22. A rechargeable battery or low voltage feed from the imaging system supplies power to the transmit circuit 14.

The transmit circuit 14 generates ultrasound transmit waveforms, such as pulsed waves of 1-10 cycles. Each transmit waveform is transmitted sequentially without transmissions from other transmit elements 12 and without any relative apodization. Alternatively, the transmit waveforms of each transmit element 12 are relatively delayed and apodized in sequential transmissions. The transmit elements 12 transduce the electrical waveform into an acoustic wavefront 20. The acoustic wavefront 20 is a broad wavefront, such as a plane or diverging wavefront. The transmit elements 12 generally act as point sources in one embodiment. In other embodiments, a weak focus, no focus, or a focal point on or behind the transmit array are used to generate the broad wavefront. The broad wavefront extends outward from the transmit element 12 and/or transducer housing 22 along azimuth and elevation dimensions. In alternative embodiments, the broad wavefront extends in azimuth or elevation and is focused more narrowly, such as an at least part converging wavefront, in the other of elevation or azimuth.

The receive array 16 is an array of PVDF or capacitive membrane elements. PVDF or capacitive membranes may not be as effective as piezoceramics for relatively high powered transmit operations. However, PVDF or capacitive membranes may operate more efficiently for receive only purposes. PVDF for example is several times more efficient on reception than PZT (e.g., Yr=1.35 vs Yr=0.2). The achievable bandwidth with these devices likewise may be significantly higher than that of piezoceramics. Alternatively, the receive array 16 includes piezoelectric elements. Singe or multiple layer elements may be used.

In one embodiment, the receiving array 16 is a sheet of PVDF with electrodes selectively applied to form an N by M array. N and M are greater than 1. Dicing operations for the receive array 16 may be avoided since the elements are defined by lithography and/or electrode deposition. Finer pitch and higher frequency receive arrays 16 may be provided.

The sheet entirely fills the region between the transmitting elements 12. Alternatively, the receiving array 16 entirely covers the transmitting elements 12 and the regions between the transmitting elements 12 as shown in FIG. 3. Through selection of materials and/or thickness, the receive array 16 of FIG. 3 is effectively or substantially transparent to the transmit pressure signal, and the receive array elements are effectively backed by intermediate layers between the transmit elements 12 and the PVDF layer of the receive array 16.

In another embodiment, the receive array 16 is a capacitive membrane ultrasonic transducer (cMUT) with N by M elements. The cMUT is formed by integrated circuit fabrication processes. Other microelectromechanical devices may be used, such as flexible beams. Each of the receive elements in the cMUT array has one or more, such as up to several hundred, cavities covered by a thin membrane. In one embodiment, the cavities within each receive element have varying dimensions, so are sensitive to different incoming pressure levels with the same bias voltage applied. Such an arrangement is disclosed in U.S. Pat. No. 7,589,456 (Publication No. 2006/0279174 (application Ser. No. 11/152,632 filed Jun. 14, 2005)), the disclosure of which is incorporated herein by reference. A digitized version of the incoming radio frequency acoustic signal with up to 8 bit resolution is output from each of the N by M receive elements. In other embodiments, the cMUT receive elements operate as analog devices.

Figure 7:
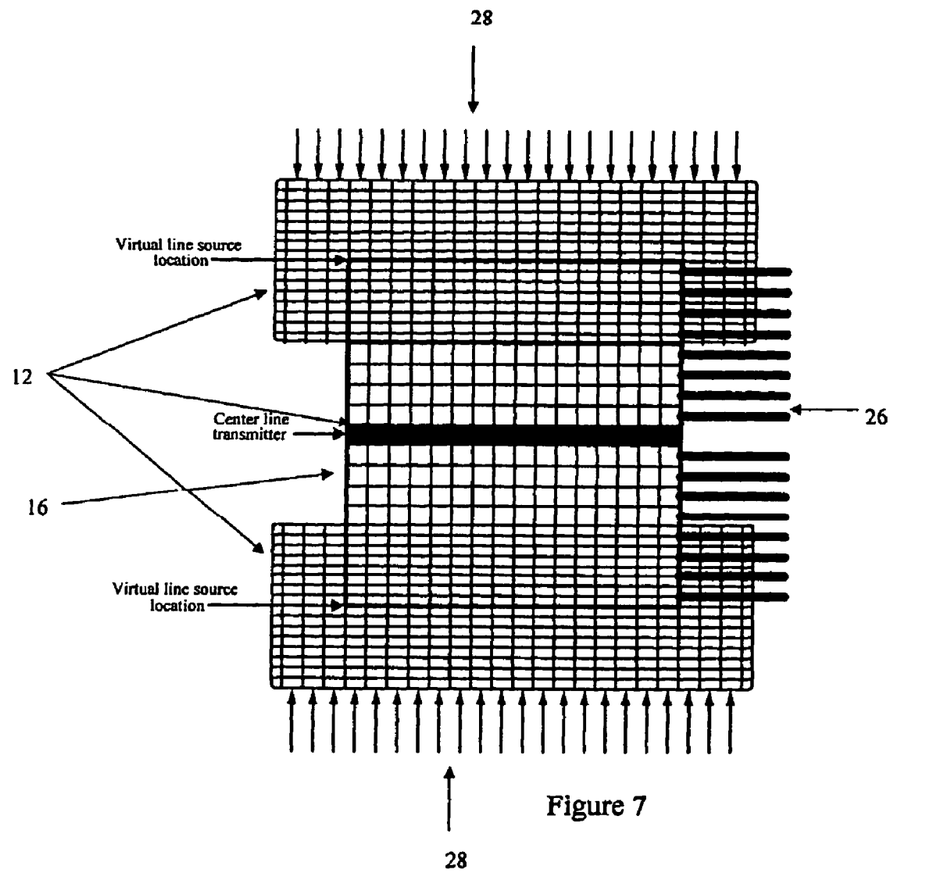

The elements of the receive array 16 are distributed in a rectangular, hexagonal, triangular or other grid. The receive array 16 is rectangular, square, cross-shaped, circular, oval or other shape. The elements are along both azimuth and elevation dimensions. The receive array 16 is flat or curved. Multidimensional arrays include two-dimensional, 1.25, 1.5, 1.75 or other arrays in any distribution of elements along two dimensions. The receive array 16 is fully sampled, but sparse or substantially fully sampled receive arrays may be used. Fully sampled receive arrays 16 may include internal locations for transmit elements 12, such as shown in FIG. 7.

The receive array 16 and receive elements are separate from the transmit elements 12. The receive elements are free of possible electrical connection to the transmit circuit, and the transmit elements are free of possible electrical connection to the receive circuit. For example, the transmit elements 12 are dedicated to transmit operation without a transmit/receive switch or other isolation circuits allowing connection of the transmit elements 12 to the receive circuit 18. Separating the transmit elements 12 from the receive array 16 may eliminate the need for signal isolation electronics or methods. The transducer is segregated into high-power transmitters and high-sensitivity receivers without compromise to use the same elements for both transmit and receive operation.

The receive circuit 18 includes one or more preamplifiers, multiplexers, mixers, delays, multipliers, phase rotators, summers, buffers, memories or combinations thereof. The receive circuit 18 electrically connects with the receive elements of the receive array 16 in a plurality of channels. PVDF and cMUT receive arrays 16 are directly grown on to silicon integrated circuits containing the receive pre-amplifiers. Alternatively, monolithic integration is used, such as growing the arrays 16 directly on top of electronics. By eliminating the necessity for transmit electronics from the same chips, the surface area of a single electronic receive channel may be on par with an acoustic receive element. Flexible circuit, z-axis backing blocks, wire jumpers, cables or other electrical connections between the elements of the receive array 16 and the receive circuit 18 may be used.

The receive circuit 18 also includes a summer, multiplier, filter and/or memory (e.g., look-up table) operable to combine data representing a same volume and responsive to the sequential transmissions. Channel data or beamformed data prior to or after detection is combined. The data representing the same or substantially same spatial locations from different transmissions is combined to synthesize the aperture.

In one embodiment, the elements of the receive array 16 connect to electronics of the receive circuit 18 positioned near (e.g., flip chip bonding or within the transducer housing 22) the array for pre-amplification and/or impedance buffering. The receive circuit 18 may implement coarse or partial beamforming for reducing the number of channels to a quantity accommodated by the imaging system. For example, one of the channel reduction receive circuits disclosed in U.S. Publication Nos. 20050148878 and 20050148873, the disclosures of which are incorporated herein by reference, are used. In another embodiment, one of the receive circuits 18, such as a sub-array mixing circuit, disclosed in U.S. Pat. No. 7,691,063 (Publication No. 20050203392), the disclosure of which is incorporated herein by reference, is used. Other receive circuits 18 may be used, such as the circuits disclosed in U.S. Pat. Nos. 7,517,317 and 7,635,334 (Publication Nos. 20050192499 and 20050243812 (Ser. No. 10/834,779, filed Apr. 28, 2004)), the disclosures of which are incorporated herein by reference.

Using time or frequency domain multiplexing, partial beamforming, sub-array mixing or other now known or later developed techniques, the receive circuit 18 reduces the number of channels for communicating information from the transducer to the imaging system. The reduced number of receive signals are sent via coaxial cable to the system. Alternatively, full beamform processing and mixing to baseband is accomplished at the transducer array, and in-phase and quadrature data is sent to the system via cable, or digitized and transmitted wirelessly or over a wire. In the case of the digital cMUT receiving array, full or partial digital beamformation may be performed by the receive circuit 18 beneath the array or in the transducer housing 22, or the data is sent to the system via a high bandwidth digital interface like Firewire, optical fiber or WAN (802.11b).

In another embodiment, the receive circuit 18 is one of the receive circuits disclosed in U.S. Pat. No. 7,508,113 (Publication No. 20050261589 (application Ser. No. 10/982,693, filed Nov. 5, 2004)), the disclosure of which is incorporated herein by reference. The receive circuit 18 for each channel includes signal conditioning circuitry, such as a low noise amplifier, variable gain stage, anti-aliasing filter, sample and hold circuit and time-domain multiplexer. Data is output for each channel to other circuits in the transducer housing 22 or the imaging system. In other embodiments, the receive circuit 18 also includes a multiplexer, delays, phase rotators, and/or summers. For example, the receive circuit 18 is implemented on a chip or as an application-specific integrated circuit and provides partial beam formation or multiplexed data. Partial beamforming may allow the output of elevation channel data at a lower frequency than for multiplexing channel signals. The receive circuit 18 forms azimuth beams with receive delays in the under-chip electronics. Digital control of the receive circuit 18 schedules each azimuth element's delay prior to summation as a function of depth. This delay may be the same for all elements in a given azimuth column. The remaining beamformation is provided in the imaging system.

The receive circuit 18 in combination with detection and image processing provide digital reconstruction of an ultrasound volume in real-time. For example, data from many receive elements are multiplexed into high-speed analog signals for transmission to the imaging system through a practical number of interconnects. The signals are first conditioned by a matching amplifier which applies gain and bandwidth shaping defined by the input specification of the analog-to-digital converter and the characteristics of the interconnect and on-chip line output amplifier. The analog signal is then converted to a digital signal. Several analog-to-digital converters with outboard sample-and-hold circuitry may be used for a single analog line. The digital signals are demultiplexed into individual channels. The individual signals then pass into a signal processing block for demodulation to baseband, low pass filtering, decimation, and inversion of any pulse compression applied on transmit (i.e., a spiking filter). The baseband in-phase and quadrature data then enter a channel memory operating as a three-dimensional array with axes of azimuth channel, elevation channel and sample number. An array of digital signal processors beam form from the channel data. The processors may allow implementation of programmable aberration correction, correlation functions for motion correction, strain imaging and vector flow, beam-to-beam filtering for super-resolution, or adaptive artifact canceling. Alternatively, hardware based receive beamformers are used. The aperture is synthesized by circuitry in the transducer housing or in the imaging system.

A memory stores the synthesized output of these processors or beamformer. This beam memory is, conceptually, a three-dimensional array with axes of azimuth beam, elevation beam and sample number. Once a volume of data is stored in the beam memory, a display processor converts the data to the appropriate format on the screen of the imager. Examples of display processing include slicing of the data at arbitrary angles, maximum intensity projection, segmentation, speckle reduction, surface rendering, alpha blending, multiplanar reconstruction or other now known or later developed representations derived from data representing a volume or distributed along three dimensions.

The transducer housing 22 is plastic, fiberglass, metal, wood or other now known or later developed material. The transducer housing 22 is sized and shaped for hand-held use. Alternatively, the transducer housing 22 is sized and shaped for use within a patient, such as a catheter, endocavity or intraoperative probe. The transmit elements 12, the receive array 16 and at least part of the receive circuit 18 are in a transducer housing 22. For example, pre-amplifiers and other signal reduction circuitry of the receive circuit 18 are within the transducer housing 22 and the synthesis circuitry is outside of the transducer housing 22. In alternative embodiments, the receive circuit 18 is outside of the transducer housing 22. Other distributions of the receive circuit 18 may be used. The transmit circuit 14 is within, outside of or partially within the transducer housing 22.

Figure 9:
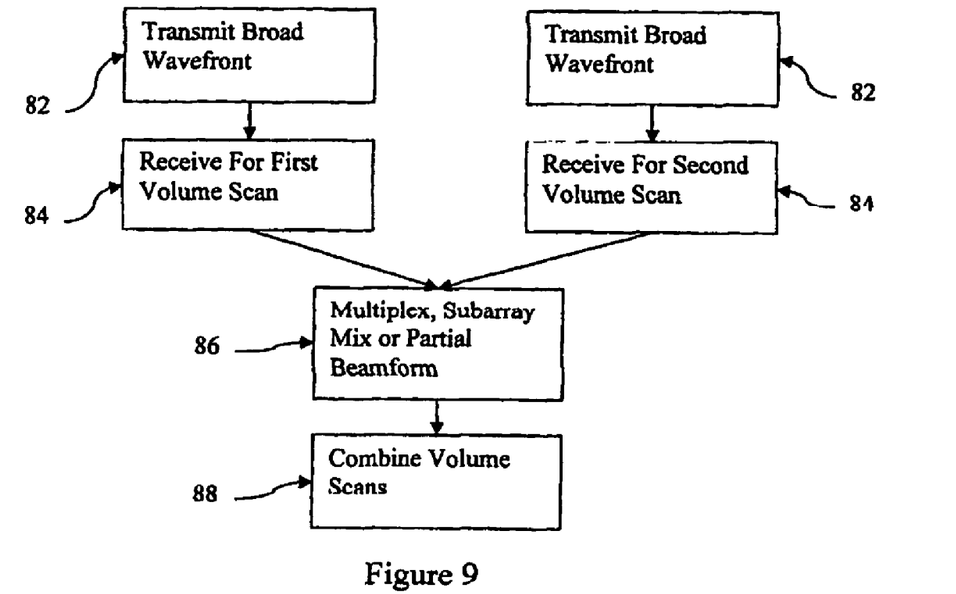
FIG. 9 is a flow chart diagram of one embodiment of a method for synthetic aperture processing with an ultrasound imaging transducer.

FIG. 9 shows a method for synthetic aperture with an ultrasound imaging transducer. A plurality of confocal data sets is acquired in response to sequential transmissions. Each confocal data set represents a same or full volume or three-dimensional region of interest. A few transmit beams impinging at different angles illuminate the region of interest. Synthetic or compound beam formation from the confocal data sets may approach the theoretical maximum spatial resolution and may provide high temporal resolution. Only a few transmit firings scan the entire volume, possibly allowing imaging speeds in excess of 1000 volumes per second.

The acts shown in FIG. 9 are performed in the order shown or a different order. The different ones of act 82 and the corresponding act 84 are performed sequentially, but may be performed simultaneously. Additional, different or fewer acts may be provided.

In act 82, acoustic energy is transmitted broadly from transmit elements. Spatially separate transmit elements generate the acoustic transmissions. Sequential use of spatially separate transmit elements results in scanning of the volume of interest from different angles. The acoustic energy wavefront passes through the volume at different angles.

The transmissions are from signal elements sequentially. For example, one transmit element 12 at one side or corner of a receive array 16 transmits broadly. Subsequently, another transmit element 12 on a different side or corner of the receive array 16 transmits broadly. In one embodiment with four transmit elements 12 or four transmit arrays, the data for synthesis is acquired in two, three or four transmit firings, such as one firing of each of the four transmit elements 12.

Alternatively, the sequential transmissions are from the same or different transmit arrays. The transmit arrays may be formed from adjacent or spaced transmit elements. For example, the transmit arrays at the corners of the receive array 16 in FIG. 4 or 6 sequentially transmit broad wavefronts. As another example, the transmit arrays or transmit elements 12 from more than one edge or corner transmit at a same time, but with coding, for sequential transmissions.

The broad wavefront is a plane wave, a diverging (spherical or cylindrical) wave or weakly focused. Omni-directional transducers may be used. Transmit elements 12 which are small as compared to wavelength generate hemispherical waves. A weakly focused or unfocused phased array or larger transmit elements 12 may output higher output pressures. The broad wavefront may emulate a virtual point source for synthesis.

Since a fewer number of transmit elements 12 are used in the transmissions of act 82, less acoustic energy may be transmitted as compared to transmission with a full array. If a traditional imager has an aperture of area $A_T$, and the area of each defocused transmit element 12 is $A_D$, the emitted power decreases by a factor of $A_T/A_D$. Moreover, the focusing gain of the transmit aperture is lost or reduced. These effects, when combined, can provide a loss of signal or poor signal-to-noise ratio. The signal-to-noise ratio may be sufficient for imaging without additional techniques. The use of PVDF or a cMUT receive array 16 may provide sufficient signal-to-noise ratio. Alternatively, the acoustic energy output by the transmit elements 12 may be increased, but may be limited by regulations or performance capability.

In one embodiment, the signal-to-noise ratio is increased by coding the transmissions as a function of transmit element. Spatial transmit coding increases transmit power for synthesized aperture. Without spatial coding, the image is formed by a summation of the data from each of the four transmit elements 12 or arrays on separate firings. Spatial coding allows transmission with two or more, such as all four, transmit elements or arrays at once. Multiple or sequential transmit firings are used, such as four transmit firings. The signal processing for data associated with each corner is separated. For example, different transmit elements 12 use inverse transmit waveforms for different transmit firings. Any now known or later developed spatial coding schemes may be used. The received data is multiplied by the inverse of the coding matrix. In one embodiment, a Hadamard matrix is used.

In another embodiment, bias variation in cMUT based transmit elements 12 performs spatial coding. Instead of receiving from a certain element selected by a multiplexer, a group of elements is selected using bias control. The polarity of transduction in a cMUT is controlled by the bias polarity. To illustrate, consider a 2×2 matrix of transmit elements 12. Over four firings, the bias polarities are switched in a pattern so that linear combinations of the received data recreate the signal from each transmit element 12. Larger processing gains can be obtained from choosing larger sub-apertures.

In another embodiment, temporal coding increases the signal-to-noise ratio. The transmit waveforms are coded, such as with chirp, Golay or Barker codes. The "spiking filter" or inverse code operation is performed on the channel data prior to beam formation. At this point in the signal processing chain, no focusing has occurred. Consequently, long time-bandwidth products may be achieved with a concomitant improvement in signal-to-noise ratio.

Additional or alternative signal-to-noise ratio improvement may be provided by motion compensation. The data from several transmitter firings is coherently combined, yielding $10 \log_{10} F$ dB of improvement if F is the number of firings added. As the number of firings for signal-to-noise ratio improvement increases, tissue motion is estimated to preserve coherence. Motion is estimated using correlations between the data sets, such as a cross-correlation or sum of absolute differences. The motion is used to align the data sets locally or globally. Coherence is maintained over the entire volume.

In act 82, each sequential transmission illuminates a volume of interest. The volume of interest is an entire field of view for imaging. Each transmission insonifies the entire field of view. The transmitted plane wave or diverging wavefront extends over azimuth and elevation dimensions. Different amounts of focus may be provided along different dimensions. For example, the wavefront may be broad for both the azimuth and elevation dimensions. Alternatively, each transmission insonifies less than the entire field, such as a quarter, more or less.

In one embodiment, sequential transmissions illuminate a same plane or volume, but different sets of sequential transmissions illuminate different planes or volumes. For example, the wavefront is more focused, such as being divergent or broad along one dimension and focused relatively narrower along another dimension. Traditional beamforming is provided along one dimension, such as in azimuth. The synthetic aperture is formed along the other dimension, such as in elevation. Each firing covers an elevation plane at a single azimuthal angle. MZ beams are needed to create a volume with focal zones, which makes the imaging speed about 50/Z volumes per second.

Figure 8:
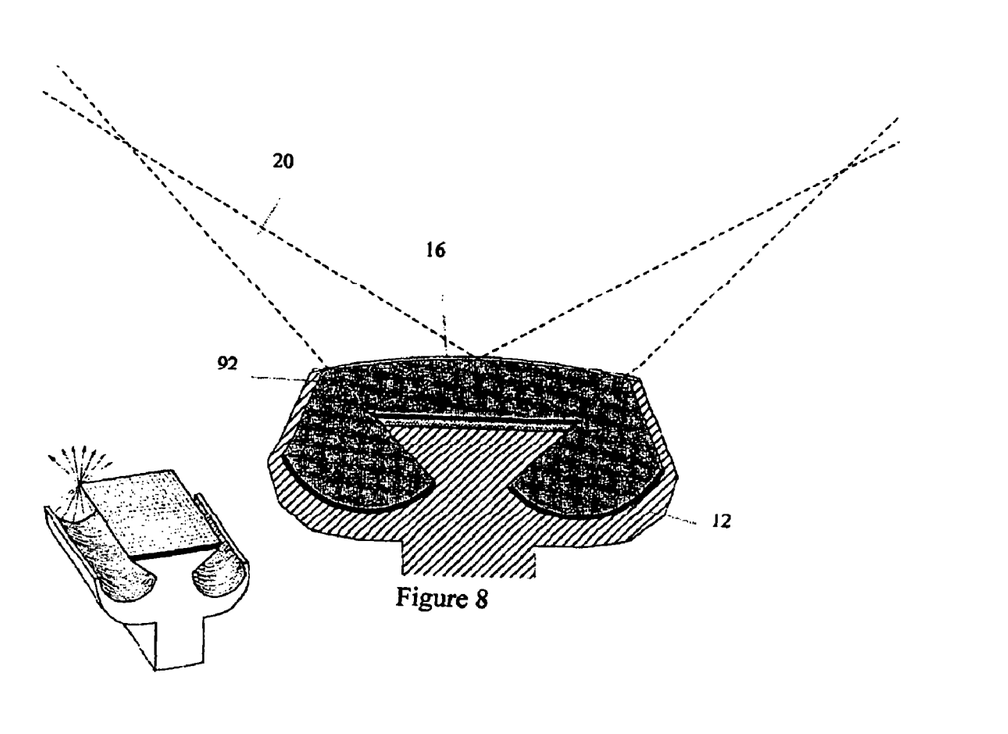
FIG. 8 is a side view of the transducer of FIG. 7.

Focus along one dimension may increase the power density of the transmission, increasing the signal-to-noise ratio. A transducer with a one-dimensional focus in azimuth and broad transmission in elevation is shown in FIGS. 7 and 8. FIG. 7 shows three linear transmit arrays of transmit elements 12. Fewer or additional arrays may be used. For example, the central transmit array of elements 12 is not provided. The center transmit array may assist with imaging tissue close to the face of the receive array 16. The center transmit array is used with the outer transmit arrays and is focused in azimuth.

The transmit arrays are phased in azimuth for azimuth focus. The transmit arrays may or may not have multiple elements along the elevation dimension. For example, the center transmit array in FIG. 7 is a one-dimensional array for broad transmit in elevation. As another example, the edge transmit arrays in FIG. 7 have a curved shape (e.g., half pipe) or relative elevation phasing for transmitting broadly along the elevation dimension. FIG. 8 shows the edge transmit arrays as curved and offset behind the receive array 16. The focal line of the transmit arrays is along an edge of the receive array 16, effectively transmitting a broad wavefront in elevation emanating from the edge of the receive array 16. A focal line or other region behind, in front, further to the side or another location may be used. For example, the receive array 16 is offset from the acoustic window or lens by about 10 mm or other distance. The volume between the transmit and receive arrays and any lens or acoustic window is filled with fluid or other acoustic matching material. The transmit array creates a tight focus at a given point in azimuth while maintaining a large angular spread in elevation. In alternative embodiments, the transmit arrays have greater or less focus. Different relative sizes of the arrays may be provided.

Phasing one of the three transmit arrays generates focused azimuth beams. One or more focal zones are chosen to cover the depth range of interest with sufficient coherence and depth of field. In elevation, the transmit arrays generate a diverging, cylindrical wave. The elevation aperture is synthesized from two or more firings, such as one from the upper line source and one from the lower source.

The channel count for the transmit array of elements 12 may be minimized using bias line polarity for defocusing. A two-dimensional array of transmit elements 12 is provided.

The bias is controlled to defocus along one or both dimensions of the array, such as disclosed in U.S. Pat. No. 7,780,597 or 7,618,373 (Publication Nos. 20060173342 or 20050119575 (application Ser. Nos. 10/819,094, filed Apr. 5, 2004, or 10/959,665, filed Oct. 4, 2004)), the disclosures of which are incorporated herein by reference. Multiple transmit firings may be used to improve the quality of the elevation line sources.

For harmonic imaging of contrast agents or free of contrast agents, increased transmit power may provide stronger second or other harmonic response. For stronger response, such as for harmonic tissue response, the transmit arrays may be more focused along the elevation dimension, such as through bias based focusing. The transducer system is used with or without synthetic aperture.

In another embodiment, broad transmit beams are more strongly focused to cover a portion of a volume rather than an entire volume or a plane. Transmit subarrays of elements 12 are distributed around and within the receive array 12. The size of each transmit subarray is small enough so as not to disrupt receive synthesis, but large enough that the lateral extent of the transmitted radiation is controlled. The wavefront is confined to the near vicinity of a block of receive lines. The receive circuitry 18 may be capable of forming receive lines simultaneously for a subset of all of the receive lines. A modicum of focal control is provided along both axes. The same group of receive lines is used for multiple consecutive transmit events with different transmit sub arrays to synthesize for the corresponding receive lines.

In acts 84, the receive array 16 receives echoes responsive to the sequential transmissions of act 82. The elements of the receive array 16 are separate from or independent of the transmit elements 12. The echoes are received with a fully sampled multidimensional receive array 16, but acquisition of data may be performed with a sparse or substantially fully sampled receive array 16. Analog waves are generated by the transducer receive elements, but digital sensing may be used.

In act 86, the number of data channels is reduced. In one embodiment, the channel data is multiplexed as a function of time, frequency or other coding. For example, data from subarrays, such as a block of elements or elements in rows, are multiplexed together onto one interconnect with the imaging system. Greater or lesser numbers of elements may be multiplexed together. Alternatively, partial beamforming or subarray mixing are used. In another alternative embodiment, the channel data is transmitted from the receive array 16 without channel reduction.

The data from the receive array 16 is processed to form samples representing a volume. For example, receive beamformation is provided by parallel beamformers, providing for simultaneous beamformation along a plurality of receive lines. Alternatively, the channel data is transformed, such as with a Fourier transform, to generate data representing the volume. Due to the sequential transmissions, two or more sets of data represent the substantially same volume or spatial locations.

In act 88, the signals responsive to the echoes of the sequential transmissions are combined. Signals representing the same or substantially same spatial location are combined. Averaging, weighted averaging, interpolation or other combination functions synthesize the data. A nearest neighbor or combination of values from adjacent spatial locations may be used. The data may be phase adjusted for coherence prior to combination. The combination occurs prior to beamformation, after beamformation and prior to detection or after detection. By synthesizing two or more confocal data sets, the volume is represented with higher resolution. To achieve exactly the same point-spread function as a focused transmit and receive apertures, the apodizing function in the synthesis is set equal to the product of the transmit and receive apodize functions of a traditional array.

In alternative embodiments, a combined transmit and receive array is used. The elements are both transmit and receive elements, so are not separate other than as a function of time. A transmit/receive switch connects each element with transmit and receive circuits sequentially. Such arrays may allow scanning of a smaller anatomical window. In another alternative, virtual lines sources for transmit are provided within the receive array or only a sub-set of the receive elements are also switchable to transmit operation. Bias line polarity defocusing may be used in the elevation aperture with delay or phase focusing in azimuth.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. A method for ultrasound imaging with a synthetic aperture, the method comprising:
   transmitting broadly from first and second transmit elements sequentially;
   receiving with a fully sampled aperture of a receive array echoes responsive to the sequential transmissions, elements of the receive array being separate from the transmit elements, the fully sampled aperture comprising receiving with the elements of the array where the elements for receiving are without an element sized or larger gap not used for receiving between the elements for receiving wherein all of the transmit elements being outside of the receive array; and
   combining signals representing spatial locations that are the same and responsive to the echoes of the sequential transmissions.

2. The method of claim 1 wherein transmitting broadly comprises transmitting with a single element, the single transmit element being the first element for a first transmission and being the second transmit element for a second transmission.

3. The method of claim 1 wherein transmitting broadly comprises illuminating a volume of interest in each sequential transmission, the volume of interest comprising at least a quarter of an entire field of view for imaging.

4. The method of claim 1 wherein transmitting broadly comprises transmitting from first and second transmit sets of elements, the first element in the first transmit set of elements and the second element in the second transmit set of elements.

5. The method of claim 1 wherein transmitting broadly comprises transmitting a plane wave or a diverging wavefront along at least the elevation or azimuth dimensions.

6. The method of claim 1 wherein transmitting broadly comprises transmitting from different angles relative to a volume of interest, and wherein receiving the echoes comprises receiving the echoes from the volume of interest along a plurality of receive beams.

7. The method of claim 1 wherein receiving comprises receiving with a PVDF film in a multidimensional array independent of the first and second transmit elements.

8. The method of claim 1 wherein receiving comprises receiving with a capacitive micromachined ultrasound transducer array, the elements of the receive array having a multidimensional distribution, the elements of the receive array independent of the transmit elements.

9. The method of claim 8 wherein receiving comprises receiving with the elements of the receive array as digital sensors.

10. The method of claim 1 wherein transmitting comprises transmitting from the first and second transmit elements within or on a same housing as and adjacent to the receive array, the first and second transmit elements being free of overlap in azimuth and elevation with the elements of the receive array.

11. The method of claim 1 wherein receiving comprises receiving with a multidimensional receive array of the elements, the elements of the receive array being PVDF or capacitive micromachined transducer elements, and wherein the first and second transmit elements comprises multiple layer piezoelectric material and are positioned adjacent an outer periphery of the receive array.

12. A method for ultrasound imaging with a synthetic aperture, the method comprising:
transmitting broadly from first and second transmit elements at different angles relative to a volume of interest;
receiving with a multidimensional receive array echoes responsive to the transmissions, elements of the receive array being separate from and not used for the transmit elements, all of the transmit elements being outside of the receive array and not within a peripheral area with a border defined by outward most elements on an outside edge of a receive aperture used for receiving with the receive array and, all of the transmit elements not adjacent to the elements of the receive array on more than two sides; and
combining signals representing spatial locations that are the same and responsive to the echoes of the transmissions.

13. The method of claim 12 wherein transmitting comprises transmitting from single elements sequentially.

14. The method of claim 12 wherein transmitting comprises transmitting multiple times from both the first and second transmit elements, the transmissions being coded as a function of the transmit element.

15. The method of claim 12 wherein transmitting comprises transmitting with acoustic energy in a plane or diverging wavefront along at least one dimension.

16. The method of claim 15 wherein transmitting comprises transmitting with the plane or diverging wavefront along azimuth and elevation dimensions.

17. The method of claim 15 wherein transmitting comprises transmitting with the plane or diverging wavefront along the one dimension and a relatively narrow focus along another dimension.

18. The method of claim 12 wherein receiving comprises receiving with a capacitive membrane transducer array or PVDF array.

19. The method of claim 12 further comprising:
partially beamforming as a function of the signals responsive to the echoes or the combined signals.

20. A method for ultrasound imaging with a synthetic aperture, the method comprising:
acquiring first and second confocal data sets in response to sequential transmissions, the first and second confocal data sets each representing a full volume, the acquisition being with a fully sampled two-dimensional aperture of a fully sampled receive array, the fully sampled aperture comprising receiving with the elements of the array where the elements for receiving are without an element sized or larger gap not used for receiving between the elements for receiving wherein transmitting with transmit elements being outside of the receive array; and
synthesizing the first and second confocal data sets.

21. The method of claim 20 wherein acquiring comprises acquiring with the fully sampled two-dimensional receive array comprises a capacitive membrane ultrasound transducer array or PVDF array and in response to transmissions from spatially separate transmit elements.

22. A transducer system for synthetic aperture in ultrasound imaging, the transducer system comprising:
at least two transmit elements;
a transmit circuit operable to cause the at least two transmit elements to transmit acoustic energy in at least two plane or diverging wavefronts, respectively, in sequential transmissions;
a multidimensional receive array of N receive elements, the receive elements separate from and not used for the at least two transmit elements, all of the transmit elements being outside of the receive array and not within a peripheral area with a border defined by outward most elements on an outside edge of a receive aperture used for receiving with receive array and, all of the transmit elements adjacent to the elements of the receive array on more than two sides; and
a receive circuit electrically connected with the receive elements, the receive circuit operable to combine data representing common locations in a same volume and responsive to the sequential transmissions.

23. The transducer system of claim 22 wherein the at least two transmit elements are adjacent to the receive array, the at least two transmit elements being less than half of N, and the receive array is substantially fully sampled.

24. The transducer system of claim 22 wherein the transmit elements, the receive array and at least part of the receive circuit are in a transducer housing.

25. The transducer system of claim 22 wherein the transmit elements and transmit circuit are operable to transmit acoustic energy in the plane or diverging wavefronts along two dimensions.

26. The transducer system of claim 22 wherein the transmit elements comprise piezoelectric elements and the receive elements comprise PVDF or capacitive membrane elements.

27. The transducer system of claim 22 wherein the receive elements being separate from the transmit elements comprises the receive elements being free of possible electrical connection to the transmit circuit and the transmit elements being free of possible electrical connection to the receive circuit.

28. The transducer system of claim 22 wherein the transmit elements are positioned along a periphery of the receive array.

29. An ultrasound transducer for synthetic aperture, the ultrasound transducer comprising:
a first array of elements; and
a second array of elements offset in a depth direction from the first array, the second array being behind a plane extending across a face of the first array such that the second array of elements is operable to form a diverging wavefront beyond the plane and before a scan region with a focal region closer to the first array than the second array; and
wherein all of the elements of the second array being outside of the first array.

30. The ultrasound transducer of claim 29 wherein the second array comprises a curved array with the focal region being a mechanical focus.

31. The ultrasound transducer of claim 29 wherein the second array comprises at least a linear array of the elements, the linear array operable to generate the diverging wavefront with the focal region as a function of relative delays along the linear array.

32. The ultrasound transducer of claim 29 wherein the first array comprises a two-dimensional array of receive elements and wherein the second array comprises transmit only elements.

33. The ultrasound transducer of claim 29 wherein the focal region is adjacent an edge of the first array of elements.

34. The ultrasound transducer of claim 29 wherein second array is operable to generate the diverging wavefront with the focal region in elevation and steered in azimuth, the focal regions of the steered wavefronts in azimuth being distributed along a curved or straight line.

35. The ultrasound transducer of claim 29 further comprising:
    a third array of elements offset from the first array, the third array of elements operable to form another diverging wavefront with another focal region closer to the first array than the third array, the third array being on an opposite side of the first array than the second array.

36. The ultrasound transducer of claim 29 wherein the first array comprises a multidimensional receive only array of PVDF or cMUT elements and wherein the second array comprises a curved array of piezoelectric elements.

\* \* \* \* \*